United States Patent
Maruno et al.

(10) Patent No.: US 9,045,399 B2
(45) Date of Patent: Jun. 2, 2015

(54) METHOD FOR PRODUCING METHANESULFONIC ACID ALKYL ESTER SOLUTION

(75) Inventors: Shinobu Maruno, Niihama (JP); Koichi Nakazawa, Tsukuba (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 331 days.

(21) Appl. No.: 13/582,274

(22) PCT Filed: Mar. 2, 2011

(86) PCT No.: PCT/JP2011/054698
§ 371 (c)(1),
(2), (4) Date: Oct. 10, 2012

(87) PCT Pub. No.: WO2011/108563
PCT Pub. Date: Sep. 9, 2011

(65) Prior Publication Data
US 2013/0020537 A1    Jan. 24, 2013

(30) Foreign Application Priority Data
Mar. 3, 2010   (JP) ................................ 2010-046549

(51) Int. Cl.
*C07C 309/66* (2006.01)
*C07C 303/28* (2006.01)
*C07C 303/44* (2006.01)

(52) U.S. Cl.
CPC ............. *C07C 303/28* (2013.01); *C07C 303/44* (2013.01)

(58) Field of Classification Search
CPC ................ C07C 309/65; C07C 309/64; C07C 309/63–309/66; C07C 309/00; C07C 303/26; C07C 303/28
USPC ........................................... 558/44; 252/364
See application file for complete search history.

(56) References Cited

U.S. PATENT DOCUMENTS

| 5,883,093 A * | 3/1999 | Hutchinson et al. ..... 514/210.02 |
| 2005/0234123 A1 | 10/2005 | Belli et al. |
| 2007/0292926 A1 | 12/2007 | Nishiyama et al. |

FOREIGN PATENT DOCUMENTS

| JP | 09-202763 A | 8/1997 |
| JP | 2000-219669 A | 8/2000 |

OTHER PUBLICATIONS

Machine translation of JP 09202763.*
Extended European Search Report issued Jul. 18, 2013 in corresponding European Patent Application No. 11750672.5.
Aleksander M. Kolodziejczyk and Maurice Manning, "A Convenient Method for O-Alkylation of N-Substituted Tyrosines Using a Crown Ether", Journal of Organic Chemistry, ACS, US, 1981, vol. 46, No. 9, pp. 1944-1946 (XP002029237).
Donald S. Noyce, et al., "The Solvolysis of Some Substituted Cyclohexyl Methanesulfonates", The Journal of Organic Chemistry, Feb. 1969, pp. 463-465, vol. 34, No. 2.
Ronald K. Crossland, et al., A Facile Synthesis of Methanesulfonate Esters, Journal of Organic Chemistry, 1970, pp. 3195-3196, vol. 35, No. 7.

* cited by examiner

*Primary Examiner* — Mark Kopec
*Assistant Examiner* — Haidung Nguyen
(74) *Attorney, Agent, or Firm* — Sughrue Mion, PLLC

(57) ABSTRACT

An aromatic organic solvent solution of a methanesulfonic acid alkyl ester having high thermal stability is obtained by reacting an alkyl alcohol with methanesulfonyl chloride in an aromatic organic solvent in the presence of a tertiary amine, and washing the resulting aromatic organic solvent solution of a crude methanesulfonic acid alkyl ester with an aqueous alkali metal carbonate solution. The washing is performed using the aqueous alkali metal carbonate solution having a concentration of 1 to 3 mass % in an amount of 4 to 6 parts by mass per 1 part by mass of the alkyl alcohol.

10 Claims, No Drawings

METHOD FOR PRODUCING METHANESULFONIC ACID ALKYL ESTER SOLUTION

CROSS REFERENCE TO RELATED APPLICATIONS

This application is a National Stage of International Application No. PCT/JP2011/054698 filed Mar. 2, 2011, claiming priority based on Japanese Patent Application No. 2010-046549, filed Mar. 3, 2010, the contents of all of which are incorporated herein by reference in their entirety.

TECHNICAL FIELD

The present invention relates to a method for producing an aromatic organic solvent solution of a methanesulfonic acid alkyl ester having excellent thermal stability.

BACKGROUND ART

Methanesulfonic acid alkyl esters have been widely used as production intermediates of various fine chemicals. For example, it is known that a methanesulfonic acid isopropyl ester is used as an intermediate of an agricultural fungicide.

As a method for producing a methanesulfonic acid ester such as isopropyl methanesulfonate, methods described in the following documents are known. That is, Patent Document 1 discloses a methanesulfonylation (mesylation) reaction in which an alcohol is allowed to react with methanesulfonyl chloride in an organic solvent in the presence of a predetermined tertiary amine catalyst.

Non-patent Documents 1 and 2 disclose a method of methanesulfonylation conducting by reacting an alcohol with methanesulfonyl chloride in the presence of triethylamine.

In the above production methods, excess tertiary amine that is not used for the reaction remains in the reaction mixture immediately after the reaction. In order to remove the excess tertiary amine from the reaction mixture, conventionally, the reaction mixture is washed with aqueous hydrochloric acid.

PRIOR ART DOCUMENTS

Patent Document

Patent Document 1: JP2000-219669A

Non-Patent Documents

Non-patent Document 1: Donald S. Noyce et al., "The Journal of Organic Chemistry", February 1969, Vol. 34, No. 2, pp. 463-465

Non-patent Document 2: Ronald K. Crossland et al., "Journal of Organic Chemistry", 1970, Vol. 35, No. 7, pp. 3195-3196

SUMMARY OF THE INVENTION

Problems to be Solved by the Invention

In the production methods mentioned above, it is physicochemically, economically, and industrially advantageous to use an aromatic organic solvent as the organic solvent. In addition, an aromatic organic solvent solution of a methanesulfonic acid alkyl ester obtained by using the aromatic organic solvent is required to have excellent thermal stability.

Thus, an object of the present invention is to provide a method for producing an aromatic organic solvent solution of a methanesulfonic acid alkyl ester having high thermal stability.

Means for Solving the Problems

The present inventors have conducted extensive research to solve the problems mentioned above. As a result, they have found that in a method in which methanesulfonyl chloride is allowed to react with an alcohol in an aromatic organic solvent in the presence of a tertiary amine catalyst to produce a methanesulfonic acid alkyl ester, when a reaction mixture after the reaction is washed with an aqueous alkali metal carbonate solution instead of the method in which a reaction mixture after the reaction is washed with aqueous hydrochloric acid, it is possible to obtain an aromatic organic solvent solution of an methanesulfonic acid alkyl ester having excellent thermal stability.

The present invention encompasses the following aspects.

(1) A method for producing an aromatic organic solvent solution of a methanesulfonic acid alkyl ester, which comprises reacting an alkyl alcohol with methanesulfonyl chloride in an aromatic organic solvent in the presence of a tertiary amine, and washing the resulting aromatic organic solvent solution of a crude methanesulfonic acid alkyl ester with an aqueous alkali metal carbonate solution.

(2) The method for producing an aromatic organic solvent solution of a methanesulfonic acid alkyl ester according to (1), wherein the washing is performed by using the aqueous alkali metal carbonate solution having a concentration of 1 to 3 mass % in an amount of 4 to 6 parts by mass per 1 part by mass of the alkyl alcohol.

(3) The method for producing an aromatic organic solvent solution of a methanesulfonic acid alkyl ester according to (1) or (2), wherein the aromatic organic solvent is a single solvent selected from the group consisting of mesitylene, xylene, ethylbenzene, toluene, and benzene or a mixture of two or more kinds selected from the same group.

(4) The method for producing an aromatic organic solvent solution of a methanesulfonic acid alkyl ester according to any one of (1) to (3), wherein the alkyl alcohol is a secondary or tertiary alcohol.

(5) The method for producing an aromatic organic solvent solution of a methanesulfonic acid alkyl ester according to any one of (1) to (4), wherein the amount of the tertiary amine used is 0.9 to 1.1 times the molar amount of the alkyl alcohol.

(6) The method for producing an aromatic organic solvent solution of a methanesulfonic acid alkyl ester according to any one of (1) to (5), wherein the tertiary amine is triethylamine.

(7) A method for producing an aromatic organic solvent solution of a methanesulfonic acid isopropyl ester, which comprises reacting isopropyl alcohol with 1 mol of methanesulfonyl chloride per 1 mol of the isopropyl alcohol in a single aromatic organic solvent selected from the group consisting of toluene, xylene, and ethylbenzene or an aromatic organic solvent that is a mixture of two or more kinds selected from the same group in an amount of 2 parts by mass or more per 1 part by mass of the isopropyl alcohol in the presence of 1 mol of triethylamine per 1 mol of the isopropyl alcohol, and washing the resulting aromatic organic solvent solution of a crude methanesulfonic acid isopropyl ester with a 2 mass % aqueous sodium carbonate solution in an amount of 5 parts by mass per 1 part by mass of the isopropyl alcohol.

Effect of the Invention

According to the present invention, an aromatic organic solvent solution of a methanesulfonic acid alkyl ester can be provided with improved thermal stability.

MODE FOR CARRYING OUT THE INVENTION

In a method for producing an aromatic organic solvent solution of a methanesulfonic acid alkyl ester according to the present invention (hereinafter referred to as "production method of the present invention"), typically, in a nitrogen atmosphere, a tertiary amine is added dropwise to a mixed solution obtained by dissolving an alkyl alcohol and methanesulfonyl chloride in an aromatic organic solvent, and they are allowed to react preferably at 10 to 15° C. to give an aromatic organic solvent solution of a crude methanesulfonic acid alkyl ester. The aromatic organic solvent solution of a crude methanesulfonic acid alkyl ester is washed with an aqueous alkali metal carbonate solution, thereby obtaining an aromatic organic solvent solution of a methanesulfonic acid alkyl ester.

<Reaction Step>

Examples of the alkyl alcohol include primary alcohols such as methanol, ethanol, and n-propanol; and secondary or tertiary alcohols such as isopropanol, isobutanol, and t-butanol. In particular, an aromatic organic solvent solution of a methanesulfonic acid alkyl ester obtained by a mesylation reaction of a secondary or tertiary alcohol has lower thermal stability than an aromatic organic solvent solution of a methanesulfonic acid alkyl ester obtained by a mesylation reaction of a primary alcohol. Therefore, the production method of the present invention is suitable for the production of a methanesulfonic acid alkyl ester using a secondary or tertiary alcohol.

It is preferable that the methanesulfonyl chloride is used in a nearly equimolar amount to the alkyl alcohol.

Examples of the aromatic organic solvent include aromatic hydrocarbon solvents such as mesitylene, xylene, ethylbenzene, toluene, and benzene, and they may be used alone. In addition, as the aromatic organic solvent, it is also possible to use a mixture of two or more kinds selected from the group consisting of mesitylene, xylene, ethylbenzene, toluene, and benzene.

The amount of the aromatic organic solvent used is not particularly limited. However, in terms of economical efficiency, the amount is usually 2 parts by mass or more and 10 parts by mass or less per 1 part by mass of the alkyl alcohol.

In the preparation of the mixture of the alkyl alcohol, the methanesulfonyl chloride, and the aromatic organic solvent in a nitrogen atmosphere, the order of mixing or a method for mixing is not particularly limited. For example, it is possible that the methanesulfonyl chloride is added to the aromatic organic solvent, and then the alkyl alcohol is added thereto. After addition, it is preferable to stir the liquid mixture while cooling the liquid temperature to 10 to 15° C.

Next, the tertiary amine is added dropwise to the liquid mixture preferably at a temperature of 10 to 15° C. Next, the above temperature is maintained for a fixed period of time, thereby giving an aromatic organic solvent solution of a crude methanesulfonic acid alkyl ester. With respect to the rate of the dropwise addition of the tertiary amine, because the liquid mixture generates heat with the dropwise addition of the tertiary amine, the rate that allows the liquid temperature to be maintained at 10 to 15° C. is preferable.

After the dropwise addition of the tertiary amine, stirring is performed for 1 to 8 hours to cause a reaction preferably while maintaining the liquid temperature at 10 to 15° C. The reaction time is until the time when the area percentage of the alkyl alcohol relative to the peak area of the alkyl alcohol and the methanesulfonic acid alkyl ester is preferably 2.0% or less, and more preferably 1.0% or less as measured by the gas chromatography area percentage method. In addition, the reaction time may also be determined by setting a control value for the reaction conversion ratio based on the proportions of the raw material alkyl alcohol and the produced methanesulfonic acid alkyl ester, etc. Carbon dioxide produced during the reaction can be removed from the system as necessary.

Examples of the tertiary amine include alkylamines such as trimethylamine, triethylamine, and diisopropylethylamine; dialkylanilines such as dimethylaniline and diethylaniline; and dialkylbenzylamines such as dimethylbenzylamine. These tertiary amines can be used alone, and it is also possible to use a combination of two or more kinds thereof. As the tertiary amine, triethylamine is preferable.

The amount of the tertiary amine used is usually about 0.9 to 1.1 times the molar amount of the alkyl alcohol. In the case where the alkyl alcohol is isopropyl alcohol, the amount is preferably within a range of 0.99 to 1.02 times the molar amount of the isopropyl alcohol. When the molar ratio of the tertiary amine is less than the above range, the alkyl alcohol may not be completely consumed, causing a decrease in the yield of isopropyl methanesulfonate. Meanwhile, when the molar ratio of the tertiary amine is more than the above range, the product decomposes due to excess tertiary amine that is not used for the reaction, causing a decrease in the yield of isopropyl methanesulfonate; therefore, this is undesirable.

<Washing Step>

The aromatic organic solvent solution of a crude methanesulfonic acid alkyl ester obtained above is then washed with an aqueous alkali metal carbonate solution, whereby excess tertiary amine and other side reaction products and unreacted substances can be removed from the aromatic organic solvent solution of a crude methanesulfonic acid alkyl ester.

The method for washing is not particularly limited. For example, the aqueous alkali metal carbonate solution is first added to the aromatic organic solvent solution of a crude methanesulfonic acid alkyl ester, stirred, and allowed to stand to cause separation into an aqueous layer and an organic layer. This extraction operation may usually be performed only once, but may also be repeated several times. After the separated organic layer is washed with water, the aqueous layer may be removed.

Examples of carbonates in the aqueous alkali metal carbonate solution include hydrogen carbonates of alkali metals such as sodium hydrogen carbonate, lithium hydrogen carbonate, and potassium hydrogen carbonate; and carbonates of alkali metals such as sodium carbonate, potassium carbonate, and lithium carbonate.

The concentration of the aqueous carbonate solution is preferably 1 to 3 mass %, and more preferably 1 to 2 mass %. When the concentration is less than 1 mass %, the yield of isopropyl methanesulfonate may decrease. When the concentration is more than 3 mass %, the liquid separation properties may deteriorate, and there is a possibility that the product is not removed.

The amount of the aqueous carbonate solution used is preferably 4 to 6 parts by mass per 1 part by mass of the alkyl alcohol. When the amount is less than this range, the tertiary amine hydrochloride may have insufficient solubility, and there is a possibility that complete removal from the oil layer is not performed.

<Concentration Step>

In order to concentrate the methanesulfonic acid alkyl ester in the aromatic organic solvent solution obtained through the washing step, the aromatic organic solvent is distilled off by distillation.

The distillation method is not particularly limited. Examples thereof include distillation under normal pressure, vacuum distillation, pressure distillation, thin-film distillation, and azeotropic distillation. Among them, vacuum distillation and thin-film distillation, where a mild thermal history can be reduced, are preferable.

The vacuum distillation is, for example, a method in which distillation is performed at a temperature at which the self-heating of the solution after concentration starts, preferably at a temperature of 50° C. or lower and a pressure of 3 kPa or less.

The obtained aromatic organic solvent solution of a methanesulfonic acid alkyl ester can be widely used for the production of fine chemical products typified by medicines and agricultural chemicals.

EXAMPLES

Hereinafter, the present invention will be described in detail with reference to examples. However, the present invention is not limited to the following examples.

Example

In a nitrogen-purged reaction vessel, 1 part by mass of isopropyl alcohol, 2.5 parts by mass of xylene per 1 part by mass of isopropyl alcohol, and methanesulfonyl chloride in a molar ratio of 1:1 relative to isopropyl alcohol were charged, and cooled to 10 to 15° C. Triethylamine was added dropwise to the liquid mixture in a molar ratio of 0.99 relative to isopropyl alcohol, and the mixture was further allowed to stand for 2 hours while maintaining the liquid temperature at 10 to 15° C. to give an aromatic organic solvent solution of crude isopropyl methanesulfonate.

Next, 5 parts by mass of 2 mass % aqueous sodium hydrogencarbonate per 1 part by mass of isopropyl alcohol was added to the aromatic organic solvent solution of crude isopropyl methanesulfonate. The mixture was stirred for 30 minutes while maintaining the liquid temperature at 10 to 15° C. and then allowed to stand to cause separation into an organic layer (A) and an aqueous layer. The pH of the separated aqueous layer was 6.5 to 7.8. The organic layer (A) was removed, and 1 part by mass of xylene per 1 part by mass of isopropyl alcohol was added to the remaining aqueous layer. The mixture was stirred for 30 minutes while maintaining the liquid temperature at 10 to 15° C. and then allowed to stand to remove the aqueous layer. Then, 2 parts by mass of water per 1 part by mass of isopropyl alcohol and the organic layer (A) were added to the remaining organic layer. The mixture was stirred for 30 minutes while maintaining the liquid temperature at 10 to 15° C. and then allowed to stand to remove the aqueous layer, thereby giving an aromatic organic solvent solution of isopropyl methanesulfonate. The obtained aromatic organic solvent solution of isopropyl methanesulfonate was subjected to vacuum distillation at a pressure of 3 kPa and a temperature of 50° C. or lower to distill off xylene, thereby giving a 50 mass % aromatic organic solvent solution of isopropyl methanesulfonate (yield: 82%).

The 50 mass % aromatic organic solvent solution of isopropyl methanesulfonate obtained was subjected to an isothermal measurement using a Calvet-type calorimeter C-80 (manufactured by SETARAM) under the following conditions. As a result, the heat induction time was 49.5 hours.

Measurement Sample: 50 mass % aromatic organic solvent solution of isopropyl methanesulfonate, 1.01 g Reference Sample: Alumina, 2.52 g Measurement Vessel: High-pressure standard vessel made of heat-resistant nickel alloy (Hastelloy)

Atmosphere in Measurement Vessel: Air

Measurement Temperature: Isothermal hold at 65° C.

Comparative Example

A 50 mass % aromatic organic solvent solution of isopropyl methanesulfonate was obtained in the same manner as in the example, except that 5 mass % aqueous hydrochloric acid was used in place of the 2 mass % aqueous sodium hydrogen carbonate (yield: 78%, the pH of the aqueous layer after washing with 5 mass % aqueous hydrochloric acid<1).

The 50 mass % aromatic organic solvent solution of isopropyl methanesulfonate obtained was subjected to an isothermal measurement using a Calvet-type calorimeter C-80 (manufactured by SETARAM) in the same manner as in the example. As a result, the heat induction time was 23 hours.

The results of the example and comparative example showed that the 50 mass % aromatic organic solvent solution of isopropyl methanesulfonate obtained in the example has higher thermal stability.

In addition, the comparison between the example and comparative example also shows that when a reaction product is washed with aqueous sodium hydrogen carbonate, the loss of the reaction product in the washing step is reduced, and the yield of isopropyl methanesulfonate is improved.

The invention claimed is:

1. A method for producing an aromatic organic solvent solution of a methanesulfonic acid alkyl ester, which comprises reacting an alkyl alcohol with methanesulfonyl chloride in an aromatic organic solvent in the presence of a tertiary amine, and washing the resulting aromatic organic solvent solution of a crude methanesulfonic acid alkyl ester with an aqueous alkali metal carbonate solution, wherein the washing is performed by using the aqueous alkali metal carbonate solution having a concentration of 1 to 3 mass % in an amount of 4 to 6 parts by mass per 1 part by mass of the alkyl alcohol.

2. The method for producing an aromatic organic solvent solution of a methanesulfonic acid alkyl ester according to claim 1, wherein the aromatic organic solvent is a single solvent selected from the group consisting of mesitylene, xylene, ethylbenzene, toluene, and benzene or a mixture of two or more kinds selected from the same group.

3. The method for producing an aromatic organic solvent solution of a methanesulfonic acid alkyl ester according to claim 1, wherein the alkyl alcohol is a secondary or tertiary alcohol.

4. A method for producing an aromatic organic solvent solution of a methanesulfonic acid alkyl ester, which comprises reacting an alkyl alcohol with methanesulfonyl chloride in an aromatic organic solvent in the presence of a tertiary amine, and washing the resulting aromatic organic solvent solution of a crude methanesulfonic acid alkyl ester with an aqueous alkali metal carbonate solution, wherein the amount of the tertiary amine used is 0.9 to 1.1 times the molar amount of the alkyl alcohol.

5. The method for producing an aromatic organic solvent solution of a methanesulfonic acid alkyl ester according to claim 1, wherein the tertiary amine is triethylamine.

6. A method for producing an aromatic organic solvent solution of a methanesulfonic acid isopropyl ester, which comprises reacting isopropyl alcohol with 1 mol of methanesulfonyl chloride per 1 mol of the isopropyl alcohol in a single aromatic organic solvent selected from the group consisting of toluene, xylene, and ethylbenzene or an aromatic organic solvent that is a mixture of two or more kinds selected from the same group in an amount of 2 parts by mass or more per 1 part by mass of the isopropyl alcohol in the presence of 1 mol of triethylamine per 1 mol of the isopropyl alcohol, and washing the resulting aromatic organic solvent solution of a crude methanesulfonic acid isopropyl ester with a 2 mass % aqueous sodium carbonate solution in an amount of 5 parts by mass per 1 part by mass of the isopropyl alcohol.

7. The method for producing an aromatic organic solvent solution of a methanesulfonic acid alkyl ester according to claim 4, wherein the washing is performed by using the aqueous alkali metal carbonate solution having a concentration of 1 to 3 mass % in an amount of 4 to 6 parts by mass per 1 part by mass of the alkyl alcohol.

8. The method for producing an aromatic organic solvent solution of a methanesulfonic acid alkyl ester according to claim 4, wherein the aromatic organic solvent is a single solvent selected from the group consisting of mesitylene, xylene, ethylbenzene, toluene, and benzene or a mixture of two or more kinds selected from the same group.

9. The method for producing an aromatic organic solvent solution of a methanesulfonic acid alkyl ester according to claim 4, wherein the alkyl alcohol is a secondary or tertiary alcohol.

10. The method for producing an aromatic organic solvent solution of a methanesulfonic acid alkyl ester according to claim 4, wherein the tertiary amine is triethylamine.

\* \* \* \* \*